United States Patent
Täschler et al.

(10) Patent No.: US 8,022,242 B2
(45) Date of Patent: Sep. 20, 2011

(54) PROCESS FOR PREPARING ALKALI METAL OR ALKALINE EARTH METAL TRICYANOMETHANIDES

(75) Inventors: Christoph Täschler, Termen (CH); Andreas Breuer, Saas Almagell (CH)

(73) Assignee: Lonza AG, Basel (CH)

( * ) Notice: Subject to any disclaimer, the term of this patent is extended or adjusted under 35 U.S.C. 154(b) by 0 days.

(21) Appl. No.: 12/310,601

(22) PCT Filed: Aug. 16, 2007

(86) PCT No.: PCT/EP2007/007240
§ 371 (c)(1),
(2), (4) Date: Dec. 9, 2009

(87) PCT Pub. No.: WO2008/019852
PCT Pub. Date: Feb. 21, 2008

(65) Prior Publication Data
US 2010/0094040 A1    Apr. 15, 2010

(30) Foreign Application Priority Data
Aug. 16, 2006 (EP) .................................. 06017027

(51) Int. Cl.
*C07C 255/05* (2006.01)
*C07C 255/06* (2006.01)
(52) U.S. Cl. ........................................ 558/467; 558/435
(58) Field of Classification Search .................. None
See application file for complete search history.

(56) References Cited

FOREIGN PATENT DOCUMENTS
WO    9829389    7/1998

OTHER PUBLICATIONS

Mayer, "Darstellung und Eigenschaften von Tetracyanmethan", Monatsh. Chem., vol. 100, p. 462-468; 1969.
Trofimenko et al., "Tricyanomethane (Cyanoform), Carbamyldicyanomethane, and Their Derivatives", J. Org. Chem., vol. 27, pp. 433-438; 1962.
Hipps et al., "The Tricyanomethanide Ion: An Infared, Raman, and Tunnelling Spectroscopy Study Including Isotopic Substitution", J. Phys. Chem, vol. 89, pp. 5459-5464; 1985.
English translation of Cox et al., "Cyanoform or Tricyanomethane—New Preparation Method", Bul. Soc. Chim. Fr., XP009085459, pp. 948-950; 1954.
English translation of Schmidtmann et al., "Some Malonitrile Derivatives", Chemische Berichte, vol. 102, pp. 1168-1175; 1886.
English translation of Grigat et al., "Reaction of Cyanic Acid Esters with Compounds Containing a Nucleophilic Carbon Atom and With 1, 3-Dipolar Agents", Chemische Berichte, vol. 98, pp. 3777-3784; 1965.
English translation of Birchkenbach et al., "The Pseudohalogen Tricyanomethyl and the Mixed Halogen Bromotricyanomethyl", Chem. Ber, vol. 62B, pp. 153-163; 1929.
English translation of Bock et al., "Photoelectron Spectra and Molecular Poperties, 110 [1,2] Tricyanmethan-Derivates X-C(CN)3", Z. Naturforsch, vol. 42b, pp. 315-322; 1987.

*Primary Examiner* — Kamal Saeed
*Assistant Examiner* — Nyeemah A Grazier
(74) *Attorney, Agent, or Firm* — Hoffmann & Baron, LLP

(57) ABSTRACT

The present invention relates to a process for preparing highly pure alkali metal or alkaline earth metal tricyanomethanides.

9 Claims, No Drawings

PROCESS FOR PREPARING ALKALI METAL OR ALKALINE EARTH METAL TRICYANOMETHANIDES

This application is the U.S. National Phase of, and Applicants claim priority from, International Application Number PCT/EP2007/007240 filed Aug. 16, 2007, and European Patent Application bearing Serial No. 06017027.1 filed Aug. 16, 2006 which are incorporated herein by reference.

BACKGROUND OF THE INVENTION

The present invention relates to a process for preparing alkali metal or alkaline earth metal tricyanomethanides having a particularly high purity, in particular a high freedom from halides.

Ionic liquids containing alkali metal or alkaline earth metal tricyanomethanides (TCMs) are important raw materials and auxiliaries in the electrical industry, for example for the production of rechargeable batteries and electronic building blocks. For these fields of application, it is necessary that the methanides used are particularly pure, in particular free of halides, in order to avoid corrosion problems and/or unwanted secondary reactions.

The preparation of tricyanomethanides is known. The cyanidation of malononitrile (MN) was first described by Schmidtmann in *Ber. Dtsch. Chem. Ges.* 1896, 29, 1168. Here, MN is deprotonated by means of sodium ethoxide in ethanol and converted into sodium tricyanomethanide by stepwise addition of chlorocyan and then crystallized from ether. Sodium tricyanomethanide is isolated in a yield of about 70% in the process.

In *Chem. Ber.* 1929, 62B, 153, Birckenbach et al. have disclosed the cyanidation of MN by means of bromocyan. Both Birckenbach et al. and Mayer et al. (*Monatsh. Chem.*, 1969, 100, 462) have described the preparation of silver tricyanomethanide which is low in halogen by admixing crude alkali metal tricyanomethanide with silver nitrate, resulting firstly in precipitation of silver chloride or silver bromide. After further addition of silver nitrate, silver tricyanomethanide could be isolated from the filtrate. Furthermore, Mayer et al. have described the reaction of silver tricyanomethanide with chlorocyan at 100° C. for 40 hours to give tetracyanomethane which was then sublimed and subsequently hydrolyzed in sulfuric acid to form ammonium tricyanomethanide. Mayer et al. obtained lithium tricyanomethanide by addition of lithium chloride to an acetonitrile solution of tetracyanomethane at −96° C.

The preparation of high-purity potassium tricyanomethanide was disclosed for the first time by Hipps et al. (*J. Phys. Chem.* 1985, 89, 5459). In this process, potassium tricyanomethanide was recrystallized ten times. To remove residual organic impurities, the potassium tricyanomethanide obtained was subsequently recrystallized twice from water. This gave a white crystalline powder which on excitation with light at 5145 Å displayed no Raman fluorescence background and was interpreted as highly pure.

The cyanidation of MN by means of bromocyan in the presence of 1,4-diazabicyclo[2.2.2]octane (DABCO®) in THF has been disclosed in WO-A-98/29389. In this process, DABCO® hydrochloride crystallizes out at −20° C. over a period of 28 hours. 98% pure lithium tricyanomethanide was obtained here.

A further process has been disclosed by Trofimenko et al. in *J. Org. Chem.* 1962, 27, 433, and in this potassium tricyanomethanide was obtained by treatment of a dihalomalononitrile-potassium bromide complex with potassium cyanide. The process gives yields of up to 60%.

In *Bull. Soc. Chim. Fr.* 1954, 948, Fox et al. have described a further process for preparing tricyanomethane at low temperature in which bromomalononitrile was reacted with potassium cyanide.

Further processes for preparing tricyanomethanides, which comprise reaction of deprotonated MN with phenyl cyanate, have been disclosed by Grigat et al. in *Chem. Ber.* 1965, 98, 3777-3784 and Martin et al. in DD-A-48614. Yields of from 75 to 88% were obtained here.

However, the known processes do not give products which are halogen-free and the products always have to be aftertreated in more or less complicated purification steps.

One process for purifying sodium tricyanomethanide by recrystallization in acetonitrile was described in 1987 by Bock et al. in *Z. Naturforsch.*, 1987, 42b, 315. Here, sodium tricyanomethanide was obtained in a yield of 70%. However, the purity obtained is not evidenced by precise information.

It was an object of the present invention to provide a simple and quick process for preparing highly pure tricyanomethanides. The process should be suitable for industrial production.

SUMMARY OF THE INVENTION

The object was achieved as set forth in claim 1.

What is claimed is a process for preparing alkali metal or alkaline earth metal tricyanomethanides having a purity of at least 99% by weight and a halide content of not more than 20 ppm, wherein, in a first step, malononitrile is converted into the corresponding alkali metal or alkaline earth metal tricyanomethanide in the presence of water and an acid by parallel addition of a halocyan or dicyan and also an alkali metal base and a pH of from 4.0 to 9.5, preferably from 6.4 to 7.7, very particularly preferably from 7.0 to 7.6, is maintained at least during the addition of the halocyan or dicyan and the alkali metal or alkaline earth metal tricyanomethanide initially formed is recrystallized from a different solvent in a second step.

It has surprisingly been found that carrying out the cyanidation at alkali metal or alkaline earth metal tricyanomethanide concentrations of from 22 to 24% by weight results in most of the alkali metal tricyanomethanide precipitating in the form of fine crystals and being able to be isolated directly as solid in a yield of about 60%.

DETAILED DESCRIPTION OF THE INVENTION

Important features of the invention are the change of solvents between synthesis and purification and also the conditions under which the reaction is carried out. The cyanidation is carried out in aqueous solution in a narrow pH range, resulting in formation of only a small amount of by-products which can then be removed very efficiently by recrystallization from a suitable organic solvent.

The malononitrile is preferably dissolved in water in the presence of a buffer system which has preferably been prepared by addition of an acid and subsequent adjustment of the pH by means of a base. Carrying out the reaction in the presence of a buffer system makes it significantly easier to maintain a narrow pH range. In a preferred embodiment, the acid is selected from the group consisting of water-miscible organic and inorganic acids, water-wettable organic and inorganic polyacids and mixtures thereof. Suitable acids are selected from the group consisting of formic acid, acetic acid, chloroacetic acid, propionic acid, 2-chloropropionic acid, 3-chloropropionic acid, toluenesulfonic acid, phosphoric acid, sulfuric acid, hydrochloric acid and nitric acid, acidic ion exchangers, polyphosphoric acid and heteropolyacids such as polymolybdic acid and polytungstic acids. Particular preference is given to using polybasic acids, very particularly preferably phosphoric acid.

The base used in the buffer system is preferably the same base which is added later in the reaction.

As halocyan, it is possible to use chlorocyan and bromocyan. Due to the presence of a pseudohalogen group, dicyan has properties comparable to chlorocyan and bromocyan. The halocyan or dicyan is particularly preferably used in a ratio to malononitrile of from 1:1 to 10:1, preferably from 1:1 to 1:3. An excess of halocyan or dicyan is particularly preferred. Preference is given to using chlorocyan.

The base in the process of the invention contains at least one alkali metal or alkaline earth metal selected from the group consisting of lithium, sodium, potassium, magnesium, calcium and barium. Preference is given to using lithium and/or sodium.

Furthermore, the alkali metal or alkaline earth metal base is particularly preferably a strong base. It is here possible to use, in particular, alkali metal or alkaline earth metal hydroxides, alkali metal or alkaline earth metal oxides or alkali metal or alkaline earth metal alkoxides. In particular, $C_{1-6}$-alkoxides can be used as alkali metal or alkaline earth metal alkoxides. In a very particularly preferred embodiment, the base is an alkali metal or alkaline earth metal hydroxide.

The alkali metal tricyanomethanide initially formed in the process of the invention has a halide content of up to 10% by weight in the first step. This solid can then be recrystallized in one step from another solvent, preferably an organic solvent. The product can be obtained as a solid from the mixture, preferably after cooling. Alkali metal or alkaline earth metal tricyanomethanides are obtained with low halide contents, a high chemical purity and in good yields of 94% by weight based on the crude alkali metal or alkaline earth metal tricyanomethanide used.

In a preferred process variant, the alkali metal or alkaline earth metal tricyanomethanide is in the second step firstly dissolved, if appropriate at elevated temperature, in methyl ethyl ketone and/or methyl isobutyl ketone and precipitated, if appropriate at a reduced temperature.

In a further preferred process variant, the alkali metal or alkaline earth metal tricyanomethanide is, if appropriate after prior addition and removal of activated carbon, precipitated in the presence of methyl tert-butyl ether or diisopropyl ether.

The recrystallization is particularly preferably carried out using the solvents acetone and methyl tert-butyl ether (MTBE).

The recrystallization is, in a preferred process variant, carried out in the presence of a porous filter aid such as activated carbon, cellulose, cotton, kieselguhr or silica sol. The alkali metal or alkaline earth metal tricyanomethanide is advantageously dissolved in the presence of the filter aid. However, the filter aid can also be added during dissolution or after the solution has been obtained. The filter material is separated off before the alkali metal or alkaline earth metal tricyanomethanide is precipitated. Particular preference is given to using activated carbon as filter aid.

The alkali metal or alkaline earth metal tricyanomethanide is preferably precipitated at a temperature below 20° C., particularly preferably 10° C. or less.

In the process of the invention, an alkali metal or alkaline earth metal tricyanomethanide having a purity of at least 99% by weight, preferably at least 99.5% by weight, particularly preferably at least 99.8% by weight, is obtained after the second step. Alkali metal or alkaline earth metal tricyanomethanides having a purity of 99.9% by weight and more can very particularly preferably be obtained. For the purposes of the present invention, the purity in % by weight is the purity of the solvent-free alkali metal or alkaline earth metal tricyanomethanides.

In the process of the invention, an alkali metal or alkaline earth metal tricyanomethanide having a halide content of not more than 20 ppm, preferably not more than 10 ppm, particularly preferably not more than 5 ppm, is obtained after the second step.

EXAMPLES

In the following examples, replacement of the sodium hydroxide by another alkali metal or alkaline earth metal base makes it possible to obtain the corresponding alkali metal or alkaline earth metal tricyanomethanides. Use of mixtures of bases of different alkali metals or alkaline earth metals also enables mixed tricyanomethanides to be obtained.

Example 1

Malononitrile (462 g, 5.95 mol, 85% strength in methanol), water (2021 g) and phosphoric acid (57.1 g, 0.5 mol, 85% strength) are mixed in a stirring apparatus. A pH of 7.5 is subsequently set by means of sodium hydroxide (50% strength). At from 25 to 30° C., chlorocyan (979 g, 15.92 mol) is introduced over a period of 2 hours, with the pH being maintained at 6.4-7.5 by regulated addition of sodium hydroxide (50% strength). A beige to brown clear solution is formed. After addition of all the chlorocyan, the reaction mixture is stirred at 25-30° C. for a further 30 minutes. During this time, the pH is maintained at 7.0-7.5 by regulated addition of sodium hydroxide (50% strength). A pH of 8.5 is subsequently set by means of sodium hydroxide. 50 g of activated carbon are then added to the reaction mixture. The suspension obtained is stirred at 25-30° C. for a further 30 minutes and subsequently filtered. 3950 g of a yellowish solution comprising 16.8% by weight of sodium tricyanomethanide, 10.5% by weight of inorganic salts, 71.5% by weight of water, 1.3 of methanol and 0.1% by weight of organic impurities are obtained as filtrate. The purity of the product is 98.6% by weight.

Example 2

Malononitrile (513 g, 6.61 mol, 85% strength in methanol), water (2021 g) and phosphoric acid (63.5 g, 0.55 mol, 85% strength) are mixed in a stirring apparatus. A pH of 7.2 is set by means of sodium hydroxide (50% strength). At from 25 to 30° C., chlorocyan (1098 g, 17.85 mol) is introduced over a period of 3 hours, with the pH being maintained at 7.0-7.2 by regulated addition of sodium hydroxide (50% strength). A beige to brown clear solution is formed. After all the chlorocyan has been added, the reaction mixture is stirred at 25-30° C. for a further 30 minutes. During this time, the pH is maintained at 7.0-7.2 by regulated addition of sodium hydroxide (50% strength). A pH of 8.5 is then set by means of sodium hydroxide and 50 g of activated carbon are added to the reaction mixture. The suspension obtained is stirred at 25-30° C. for a further 30 minutes and subsequently filtered. 4.17 kg of a yellowish solution of sodium tricyanomethanide in water having a content of 17.9% by weight of sodium tricyanomethanide are obtained. In addition, 11.0% by weight of inorganic salts, 1.0% by weight of methanol, 69.9% by weight of water and 0.2% by weight of organic impurities are present. The yield of sodium tricyanomethanide based on the malononitrile used is 100%. The purity of the product is above 98.8% by weight.

Example 3

Malononitrile (169.6 g, 2.18 mol, 85% strength in methanol), water (392.8 g) and phosphoric acid (18.8 g, 0.16 mol, 85% strength) are mixed. A pH of 7.5 is subsequently set by means of sodium hydroxide (50% strength). At from 25 to 30° C., chlorocyan (137.8 g, 2.24 mol) is introduced over a period of 4 hours, with the pH being maintained at 7.3-7.5 by regulated addition of sodium hydroxide (50% strength). After all the chlorocyan has been added, the beige to brown reaction mixture is stirred at 25-30° C. for a further 30 minutes, with the pH being maintained at 7.3-7.5 by regulated addition of sodium hydroxide (50% strength). The pH is then set to 8.5 by means of sodium hydroxide and the temperature is increased to 70° C. This results in a clear beige to brown solution being formed again from the suspension. This solution is then cooled at a rate of 6° C./h to 10° C., resulting in a suspension being formed again and this is subsequently centrifuged. 167.9 g of moist sodium tricyanomethanide having a sodium tricyanomethanide content of 72% by weight are obtained in this way. This corresponds to a yield of 49%. A further 47% by weight of sodium tricyanomethanide can be obtained from the mother liquor. Furthermore, 2.6% by weight of sodium chloride, 24.0% by weight of water and 1.2% by weight of organic impurities are present in the moist product. The purity of the product is about 98.8% by weight.

Example 4

Moist sodium tricyanomethanide as per example 3 (717 g, 4.08 mol, 64.3% strength, containing about 2.7% by weight of sodium chloride) is dried at 15 mbar and 55° C. for 12 hours, giving 519 g of dried crude product. This crude product is dissolved in acetone (3 l) at 45° C. to give a brown solution which is then admixed with activated carbon (112 g). Stirring at 25° C. for 15 minutes and subsequently filtering the mixture gives a clear slightly yellowish solution. This solution is admixed with methyl tert-butyl ether (MTBE, 9 l) and cooled to 10° C., forming a white suspension. The suspension is filtered with suction and the residue is dried at 15 mbar and 40° C. for 8 hours. White sodium tricyanomethanide (432 g, 3.82 mol, 94% yield) having a content of 99.9% by weight is obtained. The chloride content of this product is less than 5 ppm.

The invention claimed is:

1. A process for preparing alkali metal or alkaline earth metal tricyanomethanides having a purity of at least 99% by weight and a halide content of not more than 20 ppm, wherein, in a first step, malononitrile is converted into the corresponding alkali metal or alkaline earth metal tricyanomethanide in the presence of water and an acid by parallel addition of a halocyan or dicyan and also an alkali metal or alkaline earth metal base and a pH of from 4.0 to 9.5, is maintained at least during the addition of the halocyan and the alkali metal or alkaline earth metal tricyanomethanide initially formed is recrystallized from a different solvent in a second step, characterized in that the alkali metal or alkaline earth metal base contains at least one alkali metal or alkaline earth metal selected from the group consisting of lithium, sodium, potassium, calcium, magnesium and barium.

2. The process as claimed in claim 1, wherein the malononitrile is firstly dissolved in water and then mixed with an acid.

3. The process as claimed in claim 1, characterized in that the acid is an inorganic acid.

4. The process as claimed in claim 1, characterized in that the halocyan is chlorocyan.

5. The process as claimed in claim 1, characterized in that the alkali metal or alkaline earth metal base is selected from the group consisting of alkali metal and alkaline earth metal hydroxides, alkali metal and alkaline earth metal oxides and alkali metal and alkaline earth metal alkoxides.

6. The process as claimed in claim 1, characterized in that, in the second step, alkali metal or alkaline earth metal tricyanomethanide is firstly dissolved, if appropriate at elevated temperature, in acetone, methyl ethyl ketone and/or methyl isobutyl ketone and subsequently precipitated by addition of methyl tert-butyl ether or diisopropyl ether, if appropriate at a reduced temperature.

7. The process as claimed in claim 6, characterized in that, in the second step, a porous filter material is added to the alkali metal or alkaline earth metal tricyanomethanide solution and is filtered off before precipitation of the alkali metal or alkaline earth metal tricyanomethanides.

8. The process as claimed in claim 6, wherein the alkali metal or alkaline earth metal tricyanomethanide is precipitated by addition of methyl tert-butyl ether or diisopropyl ether.

9. The process as claimed in claim 1, wherein alkali metal or alkaline earth metal tricyanomethanide is obtained in a purity of at least 99.5% by weight, particularly preferably in a purity of at least 99.8% by weight.

* * * * *